United States Patent
Onuki et al.

(10) Patent No.: US 7,396,340 B2
(45) Date of Patent: Jul. 8, 2008

(54) BREAST PUMP

(75) Inventors: Zenichi Onuki, Tokyo (JP); Mitsuo Tashiro, Tokyo (JP)

(73) Assignee: Pigeon Corporation, Tokyo (JP)

( * ) Notice: Subject to any disclaimer, the term of this patent is extended or adjusted under 35 U.S.C. 154(b) by 0 days.

(21) Appl. No.: 11/084,751

(22) Filed: Mar. 21, 2005

(65) Prior Publication Data

US 2005/0234400 A1 Oct. 20, 2005

(30) Foreign Application Priority Data

Mar. 30, 2004 (JP) ............................. 2004-100283

(51) Int. Cl.
*A61M 1/06* (2006.01)

(52) U.S. Cl. ...................................................... 604/74

(58) Field of Classification Search ............. 604/73–77, 604/67, 149; 119/14.47–14.53, 14.24–14.31, 119/14.37–14.39, 14.42–14.43
See application file for complete search history.

(56) References Cited

U.S. PATENT DOCUMENTS

| | | | | |
|---|---|---|---|---|
| 1,048,481 | A | * 12/1912 | Aslakson | .................. 119/14.52 |
| 4,200,058 | A | * 4/1980 | Happel | ..................... 119/14.01 |
| 5,885,246 | A | 3/1999 | Ford | |
| 6,004,288 | A | * 12/1999 | Hochstedler et al. | .......... 604/74 |
| 6,273,868 | B1 | * 8/2001 | Nordvik | ...................... 604/74 |
| 6,387,072 | B1 | 5/2002 | Larsson et al. | ................. 604/74 |
| 6,546,893 | B1 | * 4/2003 | Happel et al. | ............. 119/14.47 |
| 6,663,587 | B2 | * 12/2003 | Silver et al. | .................... 604/74 |
| 6,673,037 | B1 | 1/2004 | Silver | |
| 2003/0139702 | A1 | 7/2003 | Renz et al. | |
| 2003/0153869 | A1 | 8/2003 | Ytteborg | |

FOREIGN PATENT DOCUMENTS

| | | |
|---|---|---|
| JP | 53-120881 | 10/1978 |
| JP | 3-101954 | 10/1991 |
| JP | 06-070722 | 10/1994 |
| JP | 08-173507 | 7/1996 |
| JP | 10-243981 | 9/1998 |
| JP | 2004-528951 | 9/2004 |

OTHER PUBLICATIONS

Search Report for JP Patent Appl. No. 2004-100283 (May 26, 2006).

* cited by examiner

*Primary Examiner*—Nicholas D. Lucchesi
*Assistant Examiner*—Theodore J Stigell
(74) *Attorney, Agent, or Firm*—Cermak Kenealy & Vaidya LLP

(57) ABSTRACT

A breast pump includes a milking port which can accommodate a breast, a storage for storing breast milk extracted from the breast, and a milking unit including a tongue section which can press the portion near an areola of the breast, and is configured in such a manner that the peak of the tongue section of the milking unit can be moved continuously in the direction away from the side of the milking port, and the height of the tongue section can be varied by independent movements of a plurality of sections of a deforming device from the side of the milking port to the inner side.

12 Claims, 13 Drawing Sheets

Side view of the breast pump
when viewed from a direction A1

Side view of the breast pump
when viewed from a direction A2

Plan view of the breast pump when viewed from a direction A3

FIG.7
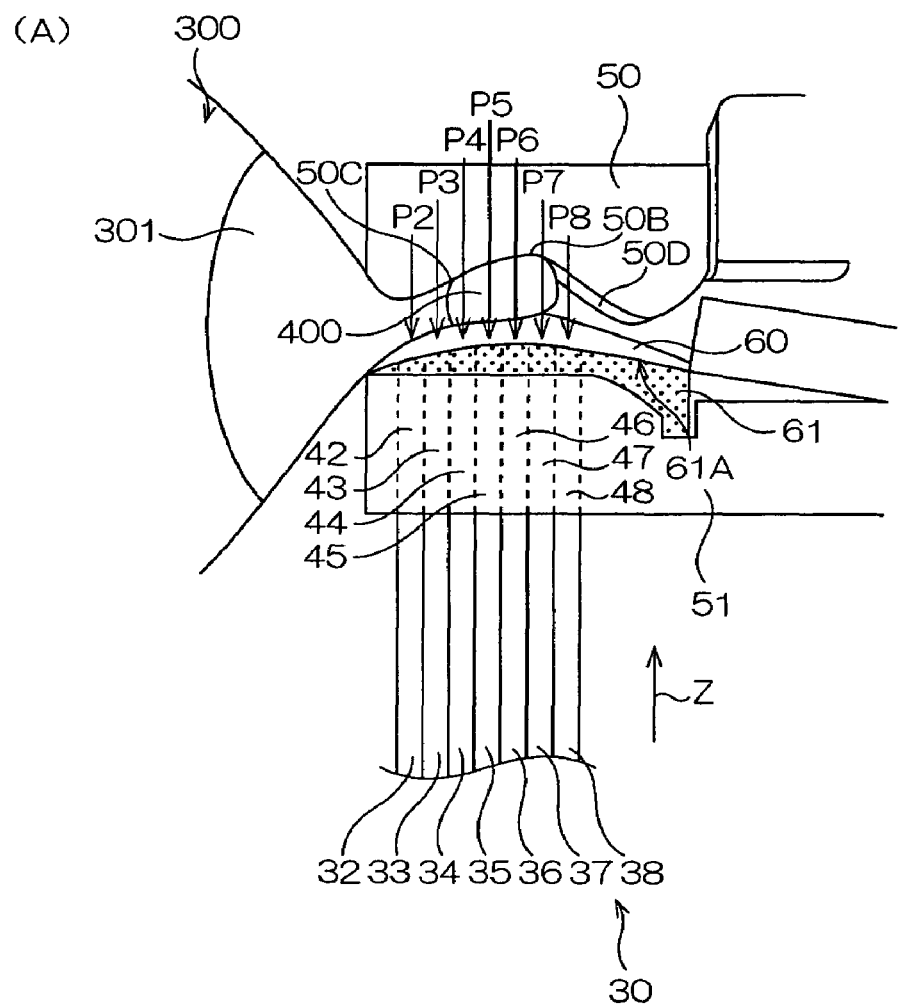
(A)
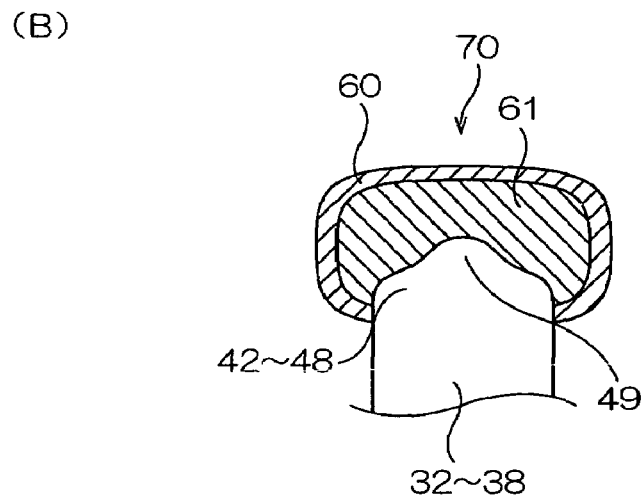
(B)

F I G. 1 1 (A)
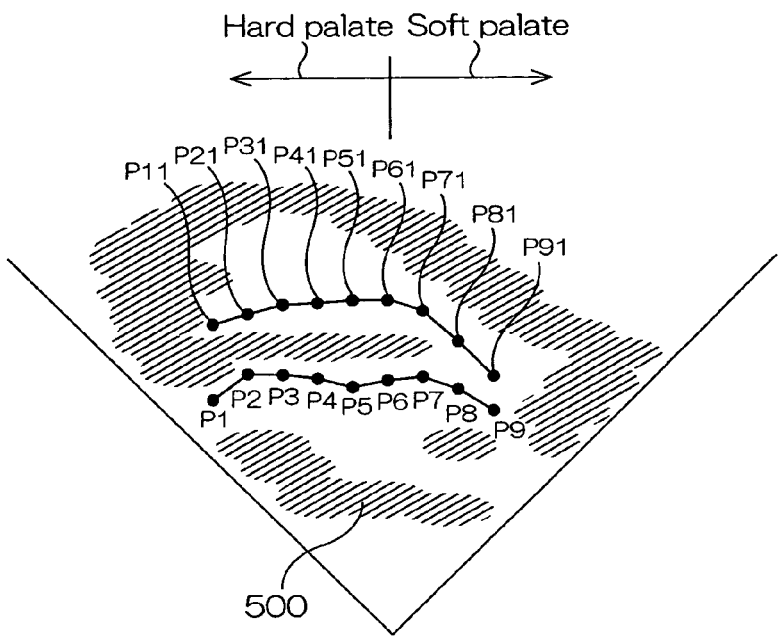
F I G. 1 1 (B)
| Variations in distance between P21 and P2 | Movement of the front half portion of the tongue |
| Variations in distance between P51 and P5 | Movement of the center portion of the tongue |
| Variations in distance between P81 and P8 | Movement of the rear half portion of the tongue |
F I G. 1 1 (C)
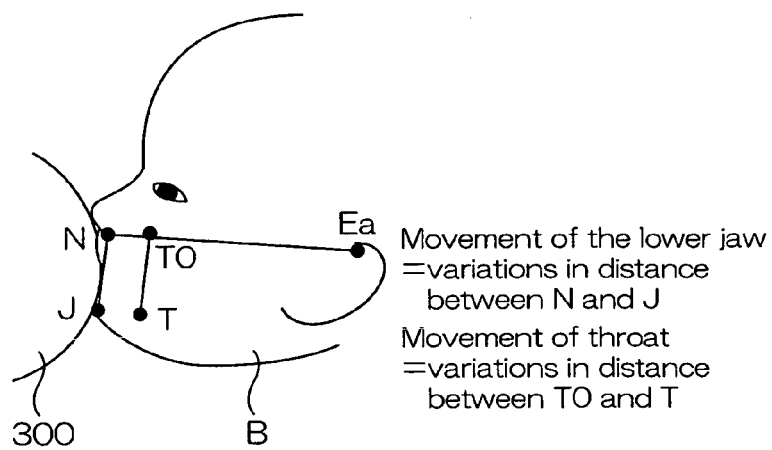

BREAST PUMP

CROSS REFERENCES TO RELATED APPLICATIONS

This invention claims the benefit of Japanese Patent Application No 2004-100283, filed on Mar. 30, 2004, which is hereby incorporated herein by reference.

BACKGROUND OF THE INVENTION

1. Field of the Invention

The present invention relates to a breast pump in which a peak of a tongue (pressing portion) can be moved stepwise for reproducing the movement of a tongue of a baby who extracts breast milk from the breast.

2. Description of the Related Art

In a breast pump for extracting breast milk in the related art, milking is carried out by pressure difference established by generating a negative pressure in the breast pump. Actual expression of breast milk is significantly affected by a pressure applied to an areola or a portion nearby. Therefore, there is a proposal of a breast pump which can press the breasts (For example, JP-T-2003-521958)

However, since actual expression of breast milk is significantly affected by application of pressure to the areola and the portion nearby as described above, development of a breast pump which can give adequate pressure stimulation to the portion near the areola when milking from the breast is desired.

SUMMARY OF THE INVENTION

Accordingly, it is a characteristic of the invention to solve the above-described problem and provide a breast pump which can reproduce an effect of pressure stimulation to a portion near an areola by a tongue of a baby to achieve adequate milking when expressing breast milk from the nipple.

In the invention, the above-described characteristic is achieved by a breast pump including a milking port which can accommodate a breast, a storage for storing breast milk extracted from the breast, and a milking unit including a tongue which can press the portion near an areola of the breast, wherein the peak of the tongue of the milking unit can be moved continuously in the direction away from the side of the milking port, and the height of the tongue can be varied by independent movements of a plurality of sections of a deforming device from the side of the milking port to the inner side.

According to the structure of an embodiment of the invention, the milking port can accommodate the breast. The storage can store breast milk extracted from the breast. The milking unit includes a tongue section which can press the portion near the areola of the breast.

The deforming device includes a plurality of sections from the milking port toward the inner side, and is adapted in such a manner that the respective sections vary the height of the tongue section continuously by the independent movement. With this deforming device, the peak of the tongue section of the milking unit can move continuously from the side of the milking port in the direction away from the milking port. Accordingly, in view of the fact that the expression of breast milk from the nipple is significantly affected by the pressure stimulation by a tongue of a baby to the portion near the areola by the nature of things, the embodiment of the invention is adapted to provide a kinetic momentum so as to give such a stimulation to an adequate position at an adequate height or cycle.

In the invention, it is preferable to provide at least a negative pressure generating unit to generate a negative pressure in the milking port, whereby the negative pressure generating unit generates a negative pressure by pulsation according to variations in the milking unit.

According to the structure of the embodiment of the invention, the negative pressure generating unit generates a negative pressure at least at the milking port for extracting milk. The negative pressure generating unit generates a negative pressure by pulsation according to variations in the milking unit.

Accordingly, the negative pressure generating unit may be adapted, for example, to increase the negative pressure before and after the peak of the pressure of the tongue section reaches a position closest to the tip of the nipple in conjunction with the pressure from the tongue section.

According to the invention, it is preferable to include a lower jaw member provided with the tongue section in the milking unit, so that the lower jaw member of the milking unit is adapted to be capable of varying the position in association with the movement of the peak of the tongue section.

According to the structure of the embodiment of the invention, the tongue section is disposed on the lower jaw member. In other words, the lower jaw member is capable of varying in position in association with the movement of the peak of the tongue section.

Accordingly, the position of the lower jaw member which corresponds to the tongue can be varied corresponding to the displaced positions of the jaw of the baby during suckling.

In the invention, it is preferable to form an upper jaw member to which the upper surfaces of the breast, the areola, and the nipple come into contact into a depressed shape of substantially semi-sphere on the inner side in comparison with the side of the milking port.

According to the structure of the embodiment of the invention, the upper jaw member to which the upper surfaces of the breast, the areola and the nipple come into contact is formed into a semi-spherically depressed shape on the inner side in comparison with the side of the milking port. Accordingly, the shape of the nipple to be sucked can be changed into a shape similar to the one in deforming the areola and the nipple when the baby catches the nipple in his/her mouth cavity corresponding to the suckling pit of the baby.

In the invention, it is preferable to provide a plurality of plate-shaped members disposed in parallel in the deforming device and a tongue member formed of resilient member being disposed on the plate-shaped members so that the plate-shaped members can be displaced independently.

According to the structure of the embodiment of the invention, the deforming device includes a plurality of plate-shaped members. The plate shaped members are arranged in parallel. The tongue member formed of the resilient member is disposed on the plurality of plate-shaped member, and the respective plate-shaped members are capable of being displaced independently.

Accordingly, by the displacement of the respective plate-shaped members, the respective corresponding portions of the tongue member can be directly adjusted in position with ease and reliability, whereby milking in a pattern similar to an actual suckling pattern of the baby is achieved.

In the invention, it is preferable to connect the respective plate-shaped members to separate drive units respectively so as to be capable of being displaced independently.

According to the structure of the embodiment of the invention, the respective plate-shaped members are connected to the separate drive units respectively.

In this arrangement, since the respective plate members can be displaced by the separate drive units, delicate movement of the respective plate-shaped members can be reproduced.

In the invention, it is preferable to form protrusions of curved shape on the upper ends of the plate-shaped members which support the tongue member, so that the tongue member can be deformed upward by the protrusions in accordance with the upward displacement of the plate-shaped member.

According to the structure of the embodiment of the invention, the protrusions are formed on the upper ends of the plate-shaped members. Then, the protrusions push the tongue member upward in association with the displacement of the plate-shaped member.

Accordingly, when the tongue member comes into tight contact with the nipple, the protrusions can apply the pressure stimulation to the nipple via the tongue member in association with the movement of the respective plate-shaped member.

As described above, according to the invention, when expressing breast milk from the nipple, the effect of the pressure stimulation to the portion near the areola by the tongue of the baby is reproduced so that an adequate milking is achieved.

BRIEF DESCRIPTION OF THE DRAWINGS

FIGS. 7A and 7B are drawings showing an upper jaw member, a tongue member, a lower jaw member, and a deforming device;

FIGS. 11A to 11C are drawings showing ultrasonic layer radiography and the like of the tongue of the baby and the portion nearby.

DESCRIPTION OF THE PREFERRED EMBODIMENTS

Referring now to the attached drawings, a preferred embodiment of the invention will be described in detail.

Since the embodiment described below is a preferred example of the invention, there are various definitions which are technically preferable. However, the scope of the invention is not limited to these modes unless otherwise specified as to limit the invention.

Figure 1:
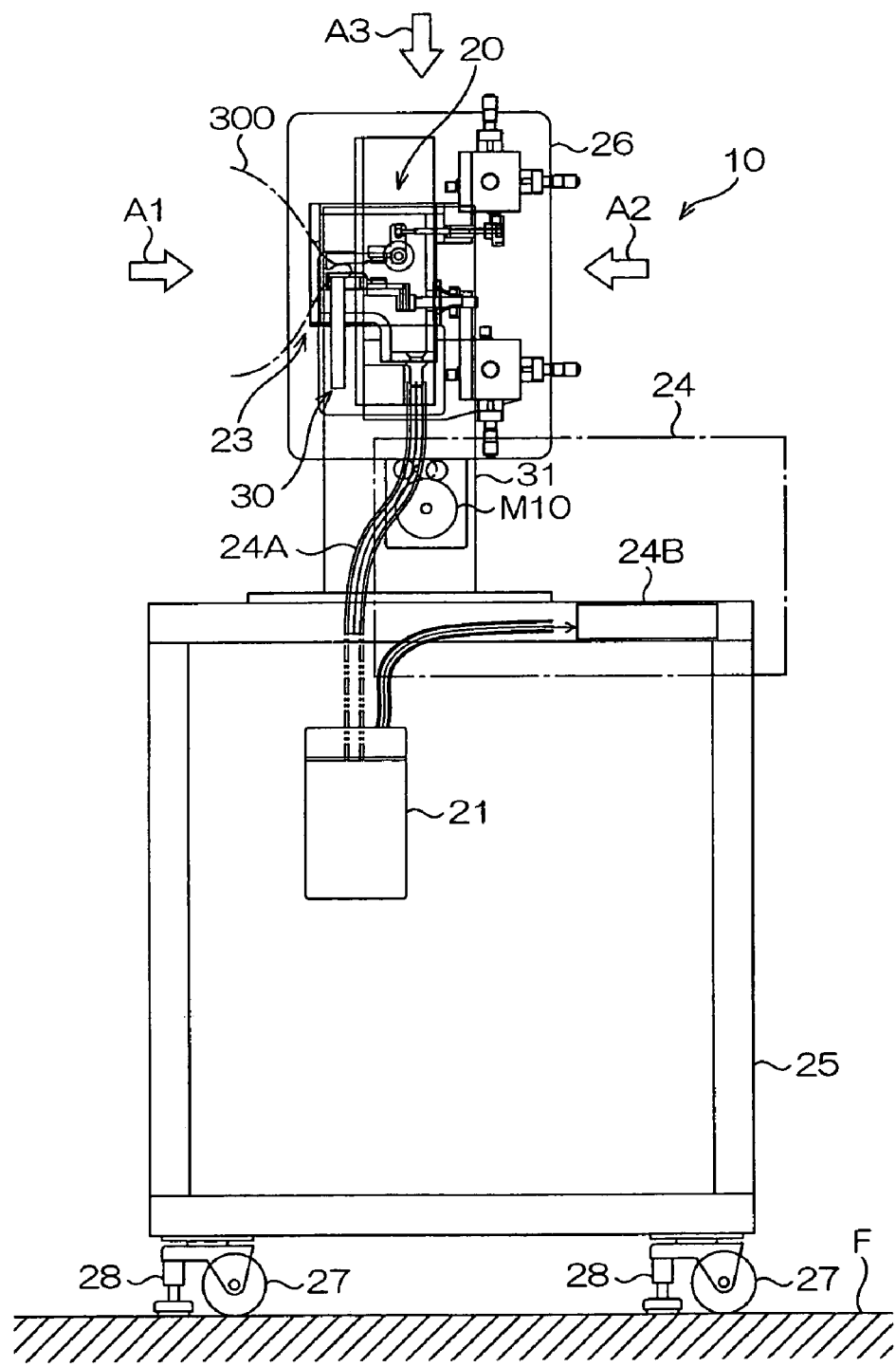
FIG. 1 is a front view showing a preferred embodiment of a breast pump according to the invention.

FIG. 1 shows a preferred embodiment of a breast pump of the invention.

FIG. 1 shows the entire breast pump 10, and this breast pump 10 can also be referred to as a milking apparatus. A characteristic of the breast pump 10 is that the peak of the tongue (pressing portion) can be moved stepwise in order to reproduce the movement of the tongue of the baby when he/she actually sucks breast milk by reflecting results of the inventor's work relating to suckling.

Based on the result of observation relating to the movement of the peak of the tongue of the baby during suckling, the breast pump 10 can reproduce the peristaltic movement corresponding to the varying numerical values of the tongue.

As shown in FIG. 1, the breast pump 10 includes a milking unit 20, a storage 21 of breast milk, a milking port 23, a negative pressure generating unit 24, a base 25, and a main body 26.

The base 25 in FIG. 1 can be supported with respect to a floor F by, for example, a plurality of rollers 27 and stoppers 28. The base 25 can move along the floor F using rollers 27 and can be fixed to the floor F using the stoppers 28.

The milking unit 20 and the main body 26 are supported on the upper surface of the base 25. The storage 21 of breast milk is stored in the base 25. The negative pressure generating unit 24 is disposed between the milking unit 20 and the storage 21. The milking port 23 is a part capable of accommodating a breast 300 during milking. The milking port 23 is provided corresponding to the milking unit 20.

Although detailed description will be made later, the milking unit 20 includes a tongue section which can press the portion near the areola of the breast 300, and is a part for extracting breast milk from the papilla. The storage 21 of the breast milk is for guiding the breast milk extracted by the milking unit 20 through a suction tube 24A and storing the same therein. The negative pressure generating unit 24 is a device for generating a space at a negative pressure in the milking unit 20 for assisting milking in conjunction with the movement of the milking unit 20.

Figure 2:
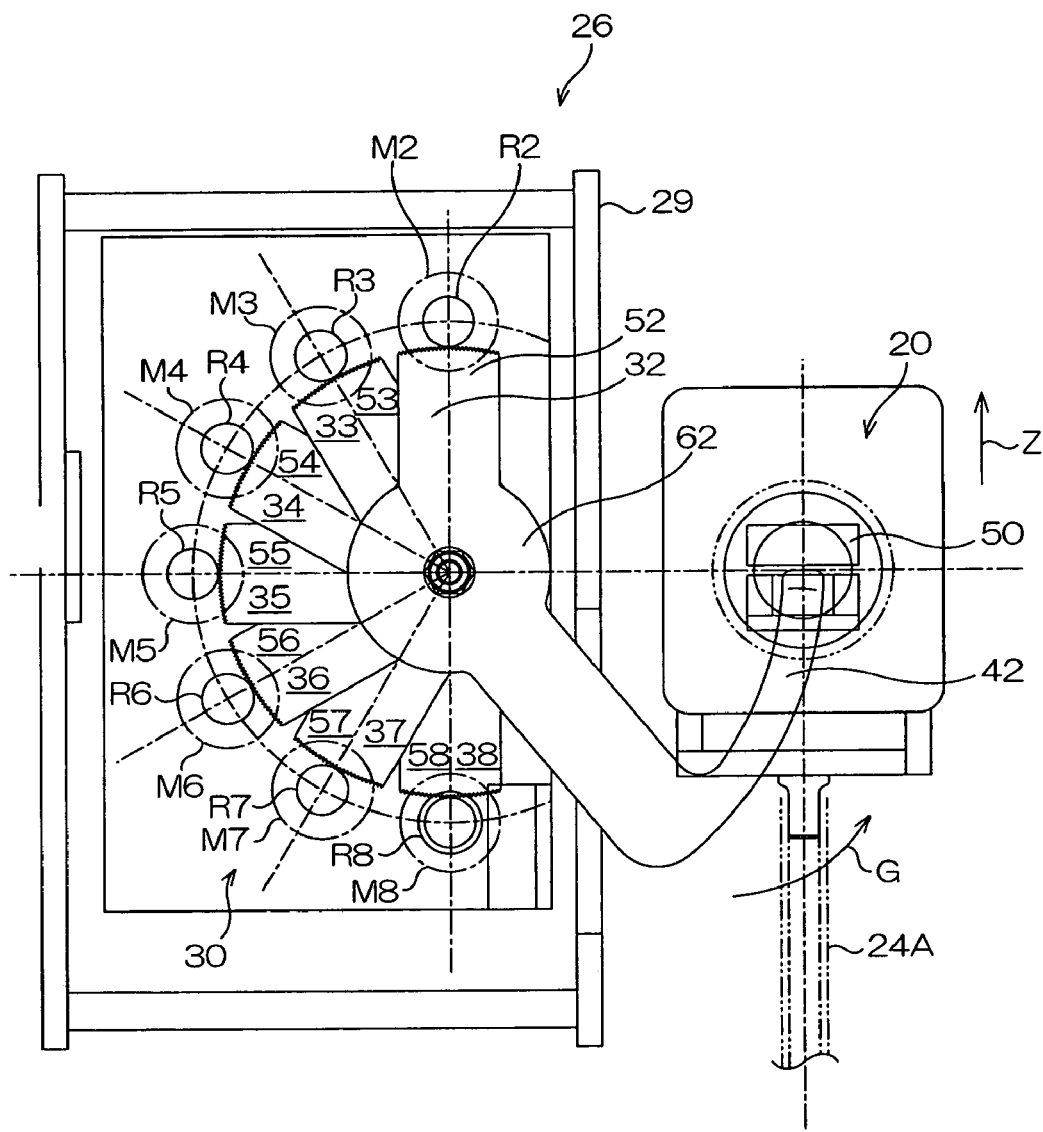
FIG. 2 is a side view of the breast pump when viewed from a direction A1 in FIG. 1.
Figure 3:
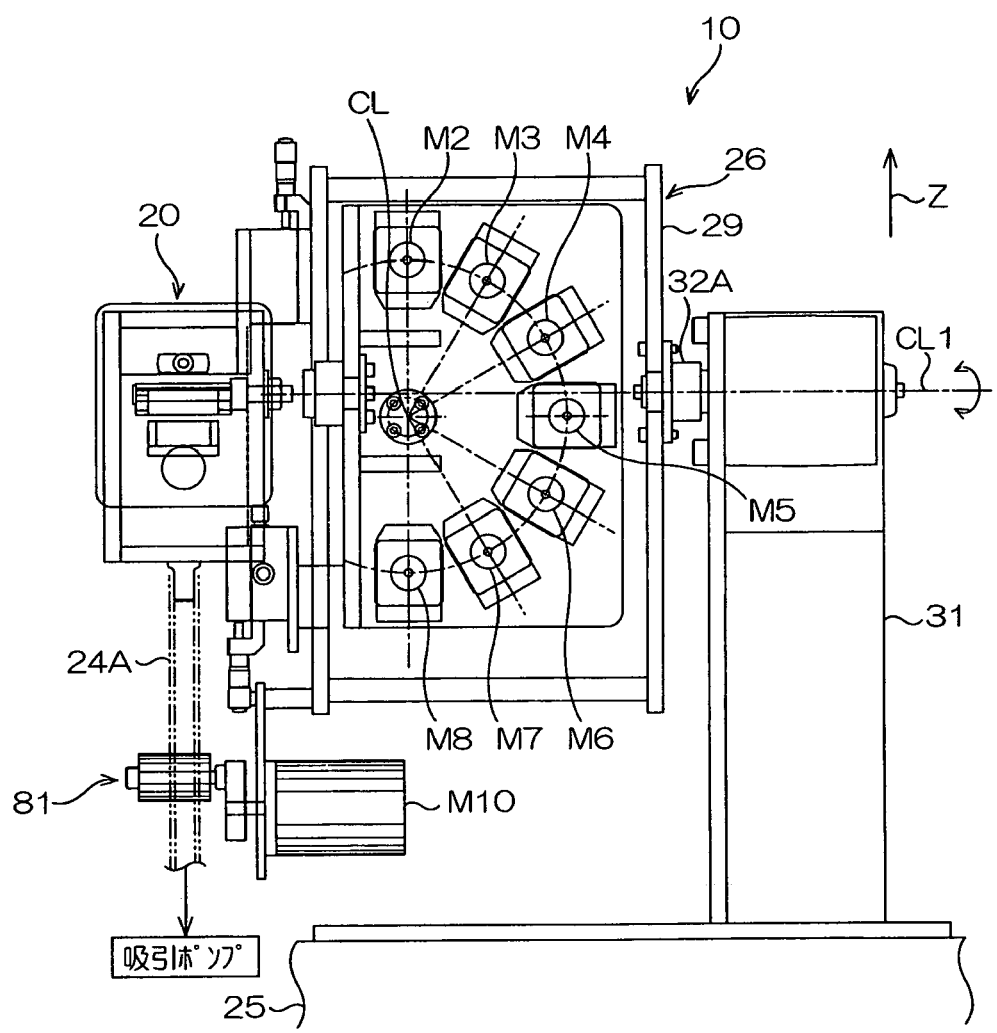
FIG. 3 is a side view of the breast pump when viewed from a direction A2 in FIG. 1.
Figure 4:
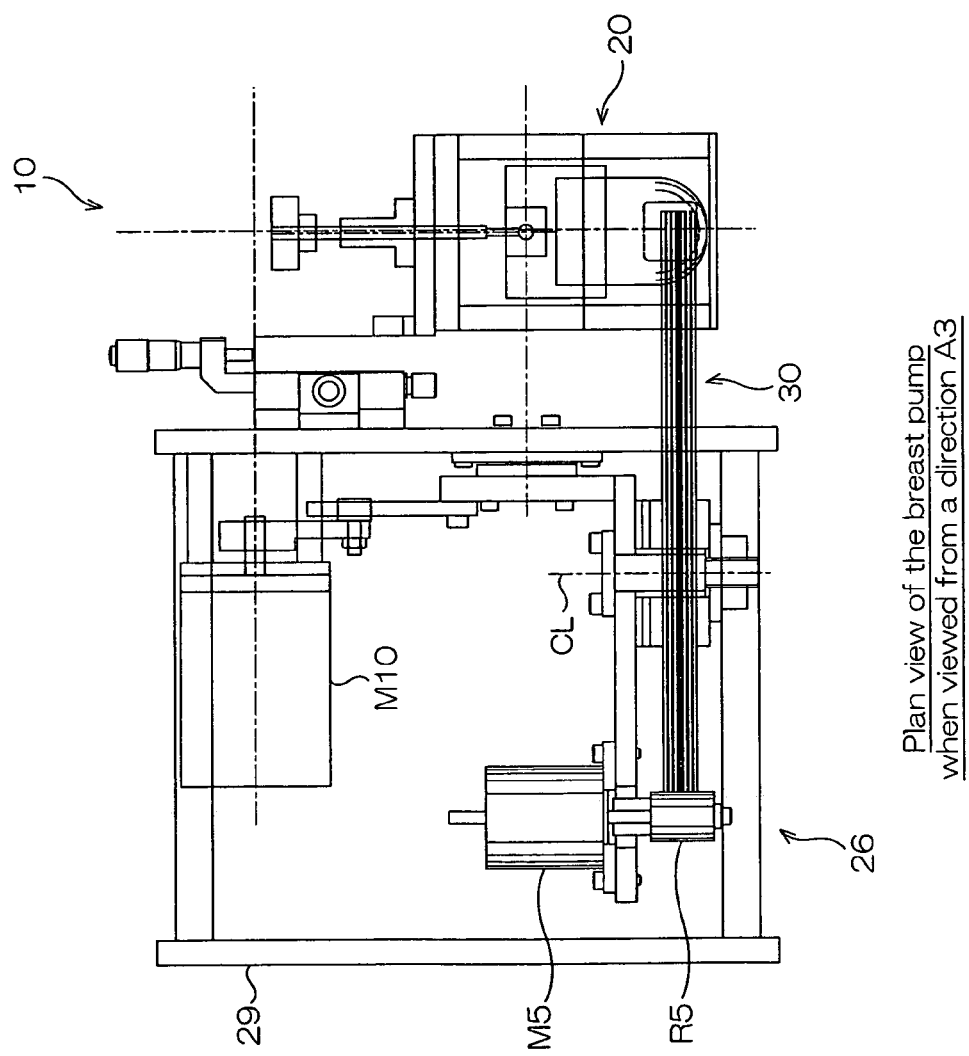
FIG. 4 is a plan view of the breast pump when viewed from a direction A3 in FIG. 1.

FIG. 2 is a side view of the milking unit 20 and the main body 26 shown in FIG. 1 viewed from the direction A1. FIG. 3 is a side view of the milking unit 20 and the main body 26 shown in FIG. 1 viewed from the direction A2. FIG. 4 is a plan view of the milking unit 20 and the main body 26 shown in FIG. 1 viewed from the direction A3.

In FIG. 2, the milking unit 20 and the main body 26 are shown. The main body 26 includes a case 29. A deforming device 30, which will be described later, is stored in the case 29. The milking unit 20 is disposed just beside the main body 26.

As shown in FIG. 3, for example, seven motors M2 to M8 are disposed at angular intervals of 30° about a centerline CL in the interior of the case 29 of the main body 26. The case 29 of the main body 26 is adapted to be changed in angle with respect to a support 31 about the centerline CL via a shaft 32A. The support 31 is fixed to the base 25, and the support 31 is provided along the vertical direction Z. Accordingly, since the angle of the milking unit 20 can be changed about a centerline CL1 together with the case 29, the adequate angle of the milking unit 20 when accommodating the breast 300 in the milking port 23 as shown in FIG. 1 is achieved.

Seven rollers R2 to R8 and seven motors M2 to M8 are accommodated in the case 29 in FIG. 2. These rollers R2 to R8 are fixed to the output shafts of the motor M2 to M8 in FIG. 3. The respective rollers R2 to R8 and the motors M2 to M8 are arranged along the circumference at angular intervals of 30° about the centerline CL.

In the plan view in FIG. 4, the motor M5 and the roller R5 are representatively shown. The milking unit 20 is mounted to the case 29 in a state in which the positional relation thereof can be adjusted.

Figure 5:
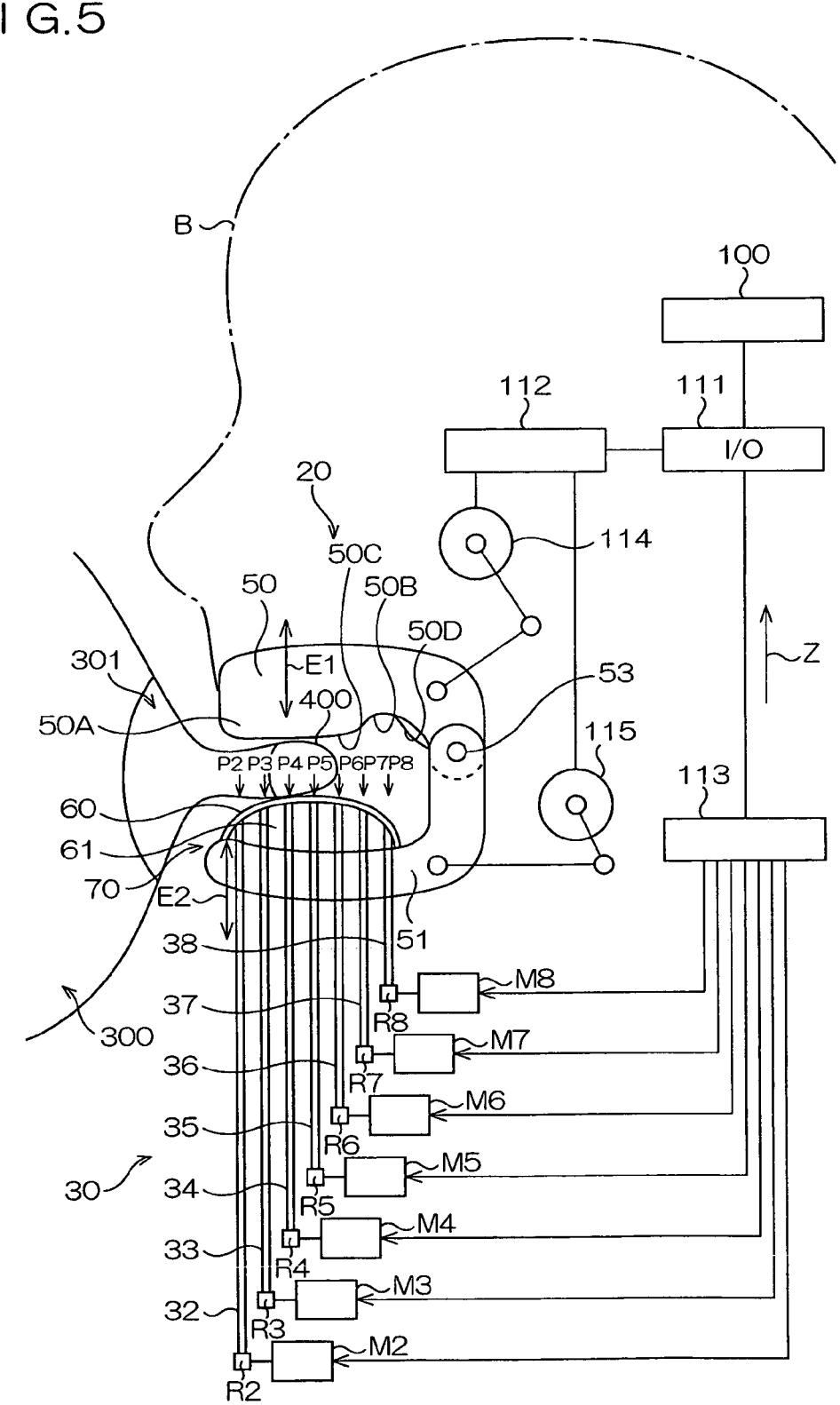
FIG. 5 is a conceptual drawing showing an example of structure of a milking unit of the breast pump.

FIG. 5 shows a structural model of the milking unit 20. The milking unit 20 includes an upper jaw member 50, a lower jaw member 51, and a tongue member 60. The milking unit 20 further includes the deforming device 30.

The upper jaw member 50 and the lower jaw member 51 are models of the upper jaw and the lower jaw of a baby B. The upper jaw member 50 and the lower jaw member 51 are adapted to be capable of rotating about a supporting member 53. When an upper jaw motor 114 is activated, the upper jaw member 50 can move in the direction E1 about the supporting member 53. Likewise, when a lower jaw motor 115 is activated, the lower jaw member 51 can move in the direction E2 about the supporting member 53.

The upper jaw member 50 shown in FIG. 5 is a part which comes into contact with the upper sides of an areola 301 or a papilla 400 of the breast 300. The upper jaw member 50 has a shape depressed on the inner side in comparison with a port side 50A. The reason why such a depressed shape is formed is to imitate the suckling pit of the baby where the tip of the papilla 400 is placed, so that the breast is deformed to a shape close to the mouth cavity of the baby. The portion from a suckling pit 50B to the port side 50A (lip side of the baby B) of the upper jaw member 50 is formed into a hard palate portion 50C formed with a resilient layer on the surface of a relatively hard material, so that the papilla 400 is reliably held while giving a soft touch to the papilla 400. In addition, a soft palate portion 50D formed of a film of resilient member on the side of the supporting member 53 with respect to the suckling pit 50B (throat side of the baby B) and adapted to be capable of deforming according to the negative pressure generated by the negative pressure generating unit 24, whereby the positional relation with respect to the tongue member 60 can be varied according to the variation in pressure or the movement of the tongue member 60.

Inside the lower jaw member 51 shown in FIG. 5, there are provided the tongue member 60 formed of a resilient member having flexibility, and a deformable intermediate member 61 which functions as the cushion member. The tongue member 60 is formed on the intermediate member 61, and the tongue member 60 and the intermediate member 61 constitute a tongue section 70. The tongue member 60 is formed of resiliently deformable material, such as silicone, elastomer, rubber, and so on.

The lower jaw member 51 on which the tongue member 60 is disposed is adapted to vary in position in association with the movement of the peak of the tongue member 60. In other words, when the deforming device 30 causes the movement of the peak of the tongue member 60 at the points P2 to P8, the lower jaw member 51 can be moved, for example, in the direction E2 in association with the movement of the peak of the tongue member 60. Accordingly, the portion corresponding to the lower jaw member 51 rotates in correspondence with the jaw of the baby during suckling.

The upper jaw motor 114 and the lower jaw motor 115 in FIG. 5 are connected to a drive unit 112. The drive unit 112 is connected to a control unit 100 via an I/O (Input/Output unit) 111.

Subsequently, a structural example of the deforming device 30 shown in FIG. 5 will be described.

The deforming device 30 includes, for example, seven plate-shaped members 32 to 38, the above-described motors M2 to M8, and the rollers R2 to R8 as shown in FIG. 3 to FIG. 5. The motors M2 to M8 may be motors, such as a stepping motor. At least five plate-shaped members are preferably formed in order to reproduce the peristaltic movement.

The motors M2 to M8 are connected to a drive unit 113. The drive unit 113 is connected to the control unit 100 via the I/O 111. The control unit 100 can control the operation of the upper jaw motor 114, the lower jaw motor 115, and the motors M2 to M8 by emitting control instructions to the upper jaw motor 114, the lower jaw motor 115, and the motors M2 to M8.

The seven plate-shaped members 32 to 38 are shown at a distance from each other in the example in FIG. 5. However, they are actually disposed almost in tight contact with each other by interposing lubricating member or lubricant therebetween. By interposing lubricant between the adjacent plate-shaped members 32 to 38, the plate-shaped members 32-38 can move smoothly with respect to each other, and smooth movement of the peak of the tongue member 60 is achieved.

Figure 6:
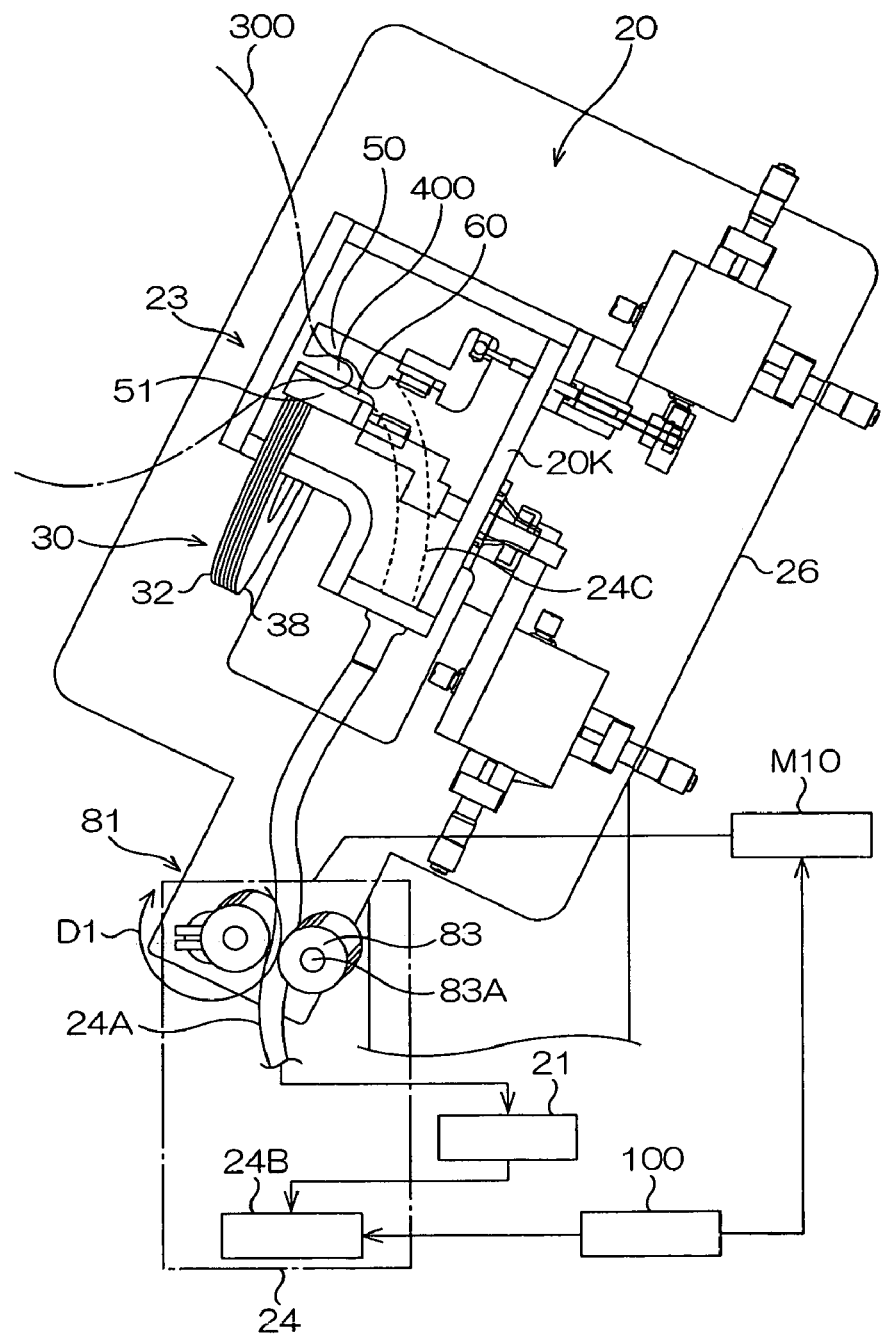
FIG. 6 is a drawing showing a milking unit, a negative pressure generating unit, and a displacing unit of the breast pump in FIG. 1.

FIG. 6 shows a part of the main body 26 and the milking unit 20, and the negative pressure generating unit (an example) 24.

The milking unit 20 is adapted so that the distal portion of the deforming device 30 can be inserted inside the milking unit 20 via the tongue member 60 or the like. In FIG. 6, the milking unit 20 is held together obliquely with the main body 26, whereby the breast 300 can be inserted into the milking port 23 and stored easily.

FIG. 7A shows the distal ends 42 to 48 of the respective plate-shaped members 32 to 38 of the deforming device 30, the upper jaw member 50, the lower jaw member 51, and the tongue member 70 in an enlarged scale. The portion from the areola 301 to the papilla 400 is in a state of being sandwiched between the hard palate portion 50C and the suckling pit 50B which are on the inner side of the upper jaw member 50 and the upper surface of the tongue member 60. The distal ends 42 to 48 of the plate-shaped members 32 to 38 come into abutment with the intermediate member 61 of the tongue section 70 at positions corresponding to the positions P2 to P8.

The distal portions 42 to 48 of the respective plate-shaped members 32 to 38 have distal end protrusions 49 respectively as shown in FIG. 7B. The tongue member 60 has a hollow shape having a width at least larger than the distal end protrusion 49, and a sponge-like intermediate member 61 is disposed in the hollow area of the tongue member 60. Accordingly, when the tongue member 60 comes into contact with the areola 301 or the like, the portion of the tongue member 60 which is in contact therewith is deformed toward the intermediate member 61, whereby the tongue member 60 comes into contact with the areola 301 or the like so as to cover from the lower side. When the distal portions 42 to 48 of the plate-shaped members are moved corresponding to the peristaltic movement, the distal end protrusion 49 comes into contact with the areola 301 or the like so as to push up in the opposite direction via the tongue section 70, whereby the same stimulation as that by the tongue of the baby is given to the areola 301 or the like.

The tongue section 70 may be provided only with the tongue member 60 without the intermediate member 61, or may be formed of a very soft solid resilient material having a hardness of about 10 to 25. It is also applicable to form the distal portions 42 to 48 into a tapered shape without forming the distal end protrusions 49.

The plate-shaped members 32 to 38 have a shape as shown in FIG. 2. The plate-shaped members 32 to 38 are assembled so as to overlap one on another along the centerline CL in FIG. 2.

In FIG. 2, the plate-shaped member 32 which corresponds to the tip of the tongue of the baby is located on the viewer's side, and the remaining plate-shaped members 33 to 38 are overlapped in sequence in the direction away from the viewer with respect to the plane of drawing of FIG. 2. The plate-shaped member 32 has the above-described distal portion 42, a drive force transmitting portion 52, and a center portion 62.

The transmitting portion 52 is a portion extending from the center portion 62 in the direction of diameter. The distal portion 42 is a portion extending from the center portion 62 in a substantially L-shape or J-shape, and is in contact with the tongue section 70. However, the distal portion 42 is rather formed into a rather arcuate shape toward the upper jaw member 50. The arcuate shape of the distal portion 42 is centered on the centerline CL.

In the same manner, the plate-shaped members 32 to 38 have the distal portions 43 to 48 shown in FIGS. 7A and 7B and the drive force transmitting portions 53 to 58. However, the directions in which the transmitting portions 52 to 58 extend are the direction toward the rollers R2 to R8. Therefore, the respective transmitting portions 52 to 58 are shifted by 30° in phase. The distal ends of the transmitting portion 52 are formed with teethed portions 59 respectively. The teethed portions 59 engage the rollers R2 to R8. Accordingly, transmission of the drive forces of the respective motors from the rollers R2 to R8 to the transmitting portions 52 to 58 without slippage is ensured.

In this manner, since the respective plate-shaped members 32 to 38 of the deforming device 30 can be displaced independently by the respective drive units including the motors and the rollers, delicate movement can be provided to the tongue section, whereby the environment of suckling done by the baby can be reproduced. Each drive unit includes one motor and one roller.

Figure 8:
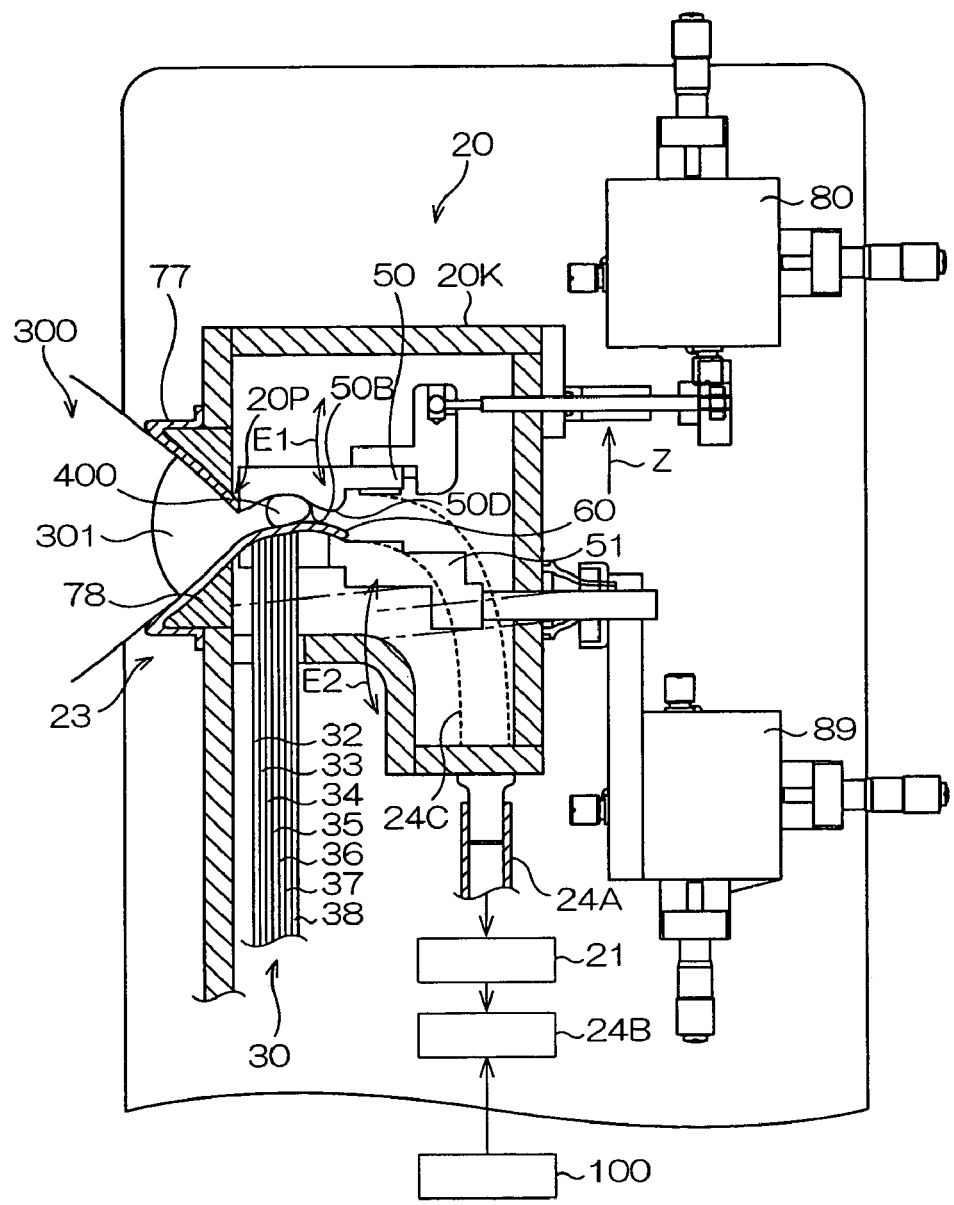
FIG. 8 is a drawing showing an example of the structure of the milking port for accommodating the breast, and the milking unit.

Referring now to FIG. 8, there is shown an enlarged view of the portion around the deforming device 30 and the milking port 23. The milking port 23 is provided on the front sides of the upper jaw member 50 and the lower jaw member 51. The milking port 23 is provided on the front side of a case 20K of the milking unit 20.

The case 20K includes a port 20P. The port 20P is provided with a trumpet-shaped contact member 77 and a cushion member 78. The trumpet-shaped contact member 77 is a member for accommodating and holding the breast 300, and is formed into a deformable layered state such as elastomer. The cushion member 78 is a member for giving a cushioning property to the breast 300 accommodated in the contact member 77, and allowing the breast 300 to fit to the port 20P, and for example, a sponge-like member may be employed.

The case 20K is formed, for example, of transparent plastic or glass in order to allow the element and the milking state in the case to be seen from the outside. The case 20K is adapted to prevent extracted breast milk from spattering out.

As shown in FIG. 8, when the breast 300 is inserted into the contact member 77 of the milking port 23, the portion from the areola 301 to the papilla 400 can be placed between the inner surface of the upper jaw member 50 and the upper surface of the tongue member 60. At this time, the borderline between the areola 301 and the papilla 400 is disposed on the deforming device 30.

The above-described upper jaw member 50, the lower jaw member 51, and the tongue section 70 are accommodated in the case 20K. The interior of the case 20K may be maintained at a negative pressure by generating a negative pressure by the negative pressure generating unit 24 via the suction tube 24A.

The negative pressure generating unit 24 can generate the negative pressure by pulsation corresponding to the variations in milking action of the milking unit 20. Accordingly, for example, it is adapted in such a manner that the negative pressure becomes higher when the peak of the tongue member 60 in the Z-direction comes to the position closest to the tip of the papilla 400.

In addition, FIG. 8 shows that an adjustment unit 80 is provided for adjusting the angle of the upper jaw member 50 in the rotational direction E1. There is also provided an adjustment unit 89 for adjusting the angle of the lower jaw member 51 in the direction E2.

Figure 9:
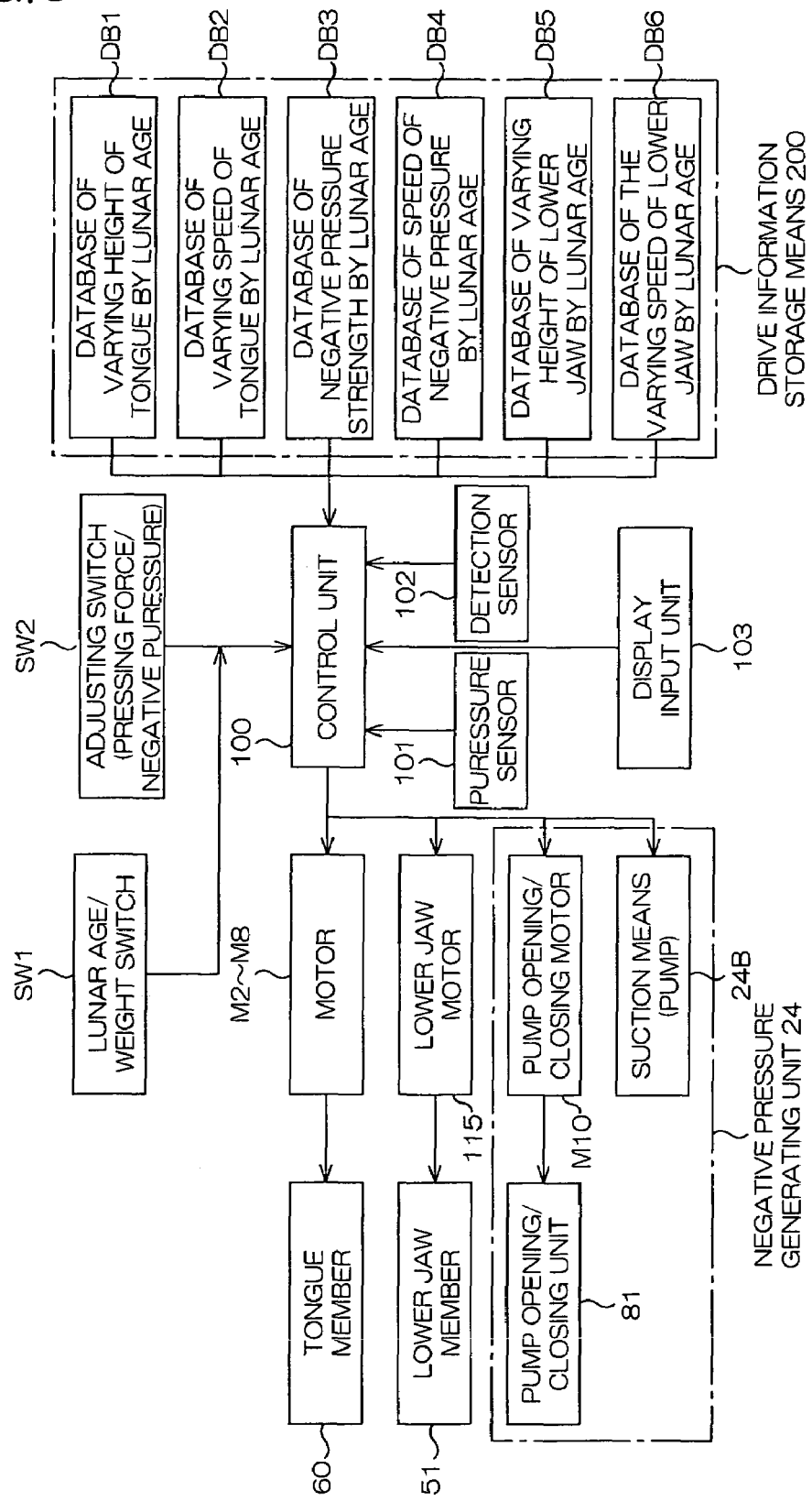
FIG. 9 is a drawing showing an example of electrical connection of the breast pump.

FIG. 9 is a block diagram showing a case in which the milking unit 10 in FIG. 1 is operated for milking.

Control unit 100 is an example of a calculating unit. The control unit 100 electrically connects a pressure sensor 101, a detection sensor 102, a display input unit 103, a lunar age/weight switch SW1, an adjusting switch SW2, a drive information storage unit 200, the motors M2 to M8, the lower jaw motor 115, and the negative pressure generating unit 24.

The pressure sensor 101 shown in FIG. 9 detects the negative pressure in the case 20K of the milking unit 20 shown in FIG. 8 and transmits the detected results to the control unit 100. The detection sensor 102 is a sensor for detecting whether or not the breast 300 is inserted into the contact member 77 as shown in FIG. 8 and, when the breast 300 is inserted into the contact member 77, transmits a signal indicating that the breast is accommodated to the control unit 100.

With the display input unit 103, the operator can select and input the setting details of the milking action or the waveforms of the milking action, for example, by touching the screen.

The lunar age/weight switch SW1 is a switch for selecting the values of lunar age and weight of the baby of a mother who receives milking operation. The adjusting switch SW2 is a switch used by the mother during operation for adjusting the pressing force of the deforming device 30 shown in FIG. 8 with respect to the tongue member 60 or for finely adjusting the negative pressure applied by the negative pressure generating unit 24.

The negative pressure generating unit 24 shown in FIG. 9 includes a pump 24B as sucking means, and a pump opening/closing motor M1 and a pump opening/closing unit 81.

FIG. 6 shows an example of the negative pressure generating unit 24.

One end of the suction tube 24A is connected to the lower end of the case 20K of the milking unit 20, and the other end of the suction tube 24A is connected to the pump 24B via the storage 21. The pump opening/closing unit 81 includes two rollers 82, 83. The roller 83 is a fixed roller which rotates about an axis 83A. The other roller 82 is a movable roller which rotates in the direction D1 and movable by the operation of a motor M10.

When the motor M10 is activated, the rollers 82, 83 can provide pulsation to the negative pressure by collapsing the intermediate portion of the suction tube 24A from the opened state to the closed state, or by changing the size of the flow path thereof.

Between the proximal sides of the upper jaw member 50 and the lower jaw member 51 to the suction tube 24A is connected by a communication tube 24C, so that a space of negative pressure is generated not in the entire case 20K, but in the portion from the milking port 23 to the suction tube 24A by the pump 24B.

Accordingly, when the pump 24B is activated, the breast milk extracted in the case 20K of the milking unit 20 can be stored in the storage 21 through the communication tube 24C and the suction tube 24A. The pump opening/closing unit 81 can generate a negative pressure in the case 20K by causing pulsation by controlling the distance between the rollers 82 and 83.

At this time, it is preferable to adapt to generate a negative pressure via a film member or a valve member so that the breast milk does not flow into the suction pump 24B.

It is also possible to connect a tube for sucking from the proximal side of the upper jaw member 50 in order to establish airflow in association with the generation of negative pressure independent from the storage 21 through which the breast milk flows instead of communicating the suction pump 24B with the milking port 23 via the storage 21. Furthermore, as means for providing pulsation, not only by the movement of the pump opening/closing unit 81, but a structure in which the suction pump 24B itself is electrically turned ON/OFF, or the negative pressure generated by the suction pump communicates with the outside air intermittently are also applicable.

Returning to FIG. 9, the drive information storage unit 200 shown in FIG. 9 will be described.

The drive information storage unit 200 includes a database DB1 of varying height of tongue by lunar age, a database DB2 of varying speed of tongue by lunar age, a database DB3 of negative pressure (suction and sipping pressure) strength by lunar age, a database DB4 of speed of negative pressure (suction and sipping pressure) by lunar age, a database DB5 of varying height of lower jaw by lunar age, and a database DB6 of the varying speed of lower jaw by lunar age, and so on stored therein.

Referring now to FIGS. 10A to 10F, an example of consecutive images of the interior of the mouth cavity of a baby in a state of performing suckling action taken by the ultrasonic layer radiographic apparatus will be shown.

When the baby drinks milk from the nipple, the suckling action is performed by the peristaltic movement of the tongue section as shown in FIGS. 10A to 10F.

Figure 10:
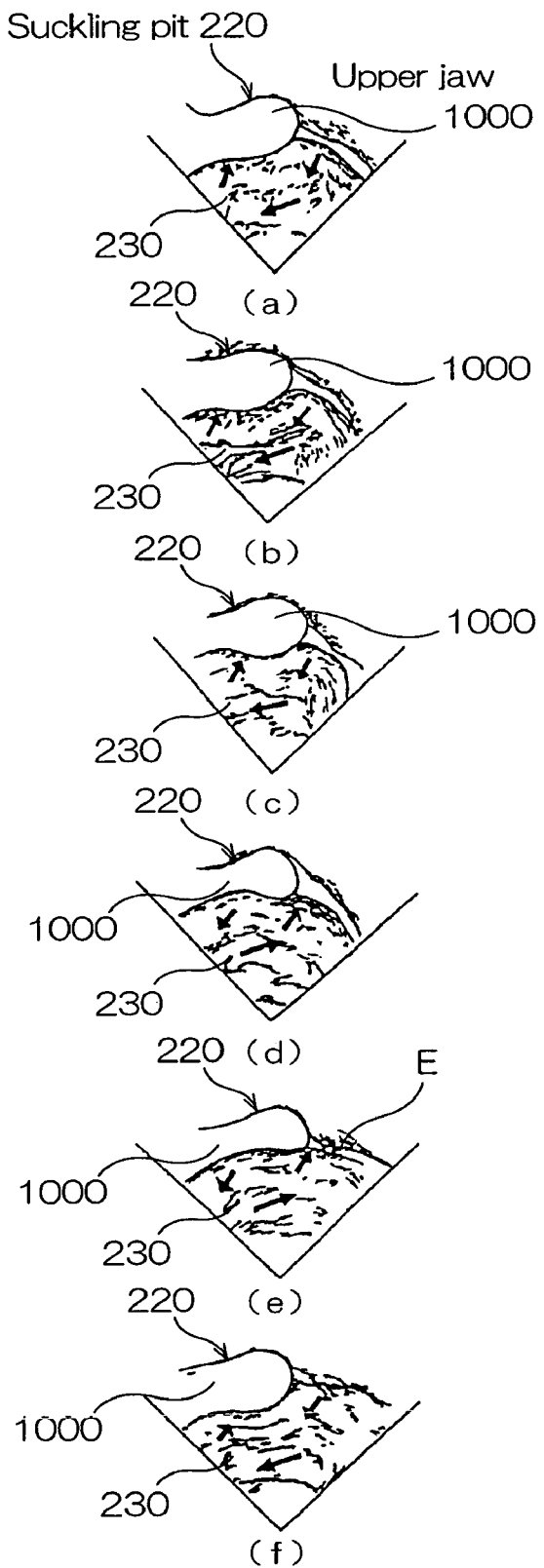
FIGS. 10A to 10F are drawings showing examples of a consecutive image of a state in the mouth cavity of a baby during a suckling action taken by an ultrasonic layer radiographic apparatus.

In FIG. 10A, the baby who performs the suckling action has a depression called a suckling pit 220. The baby has the suckling pit 220 only during period where he/she performs suckling action for milking, and it will disappear as he/she grows up.

A nipple 1000 of a mother enters into the suckling pit 220 in the mouth cavity of the baby. In this state, a tongue 230 of the baby comes into contact with the nipple 1000 from the lower side in the mouth cavity, and the sides of the tongue 230 are elevated and come into tight contact with the nipple 1000 as if it wraps therearound.

Then, as shown in FIG. 10B and FIG. 10C, the front portion of the tongue 230 is swelled upward to push the nipple 1000 from the tongue 230. This motion moves gradually toward the rear of the tongue 230 like a wave as shown in FIG. 10D to FIG. 10F.

In this process, the tongue 230 performs the peristaltic movement from the front to the rear like a wave, and the nipple 1000 is squeezed from the proximal side to the tip, and hence a closed space E is formed among the nipple 1000, the tongue 230, and the upper jaw member.

The closed space E shown in FIG. 10E is reduced as the nipple 1000 expands, and preferably, the nipple 1000 expands until the closed space E disappears. According to a series of movements, the pressure in the mouth cavity increases, and when the closed space E is opened by the subsequent peristaltic movement of the tongue 230, a negative pressure is generated, whereby breast milk is expressed toward an epiglottis of the baby vigorously. The baby drinks the expressed breast milk and the suckling action is completed.

In this manner, the baby gives stimulation to the areole or the nipple including the papilla by the peristaltic movement of the tongue 230, and generates a negative pressure in the mouth cavity effectively by expanding the nipple of the mother. In this manner, the baby tries to drink the breast milk more effectively by generating the negative pressure effectively to promote expression of the breast milk from the nipple.

Referring to the suckling action of the baby as shown in FIGS. 10A to 10F, the inventor explains an example of the movement of the tongue during the suckling action. FIG. 11A shows an example of the interior of the mouth cavity of the baby taken by the ultrasonic layer radiography.

Point P2 to point P8 are set at positions corresponding to a tongue 500. The point P2 to the point P8 are measuring points for measuring the movement of the tongue 500, and correspond to the point P2 to the point P8 shown in FIG. 7A, respectively.

As shown in FIG. 11B, the movement of the front half portion of the tongue 500 can be represented by variations in distance between a point P21 and the point P2. The movement of the center portion of the tongue 500 can be represented by variations in distance between a point 51 and the point P5. The movement of the rear half portion of the tongue 500 can be represented by variations in distance between a point P81 and the point P8.

FIG. 11C shows an example of the movement of the lower jaw and the throat. The movement of the lower jaw can be represented by variations in distance between N and J. The movement of throat can be represented by variations in distance between T0 and T. The points N, T0 can be connected by a substantially straight line with a point Ea near the ear of the baby B.

Figure 12:
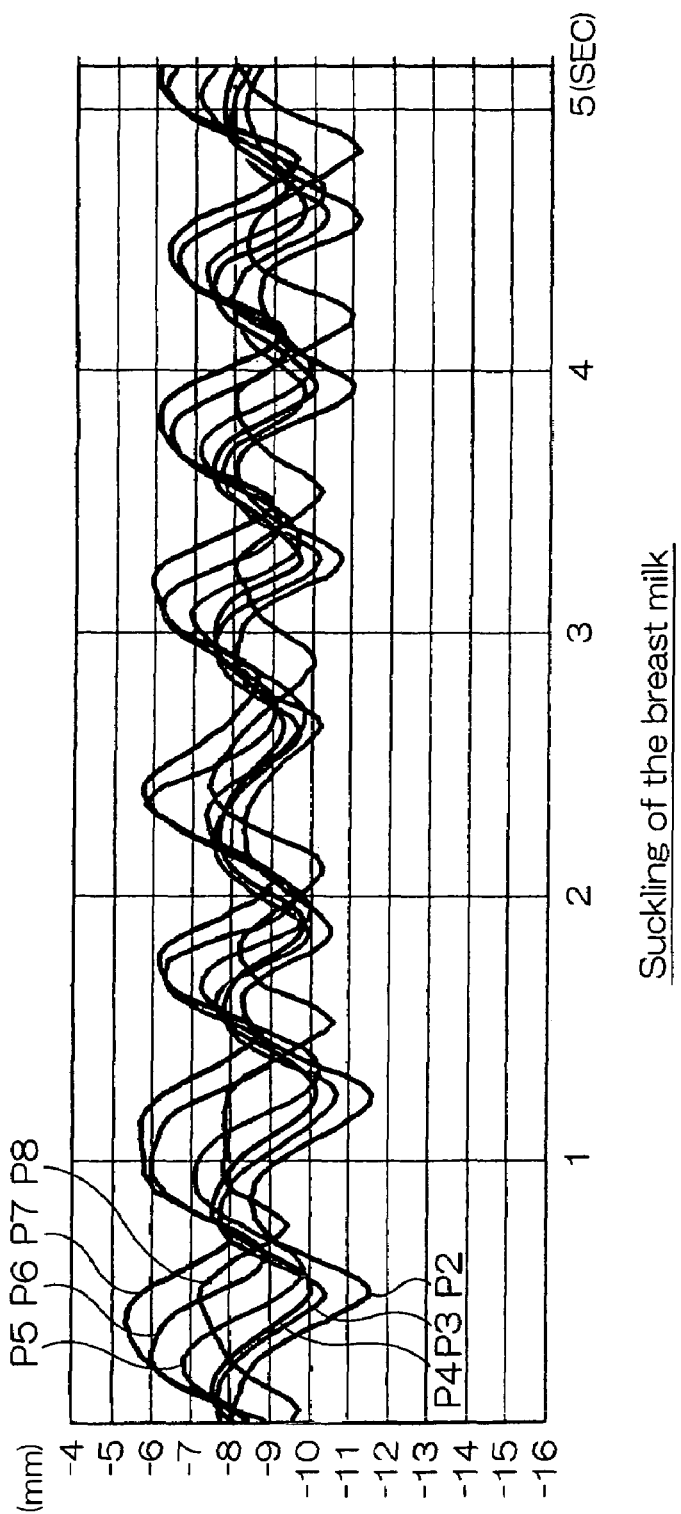
FIG. 12 is a drawing showing an example of variations in height of the tongue with time at respective points P2 to P8 on the tongue of the baby.

FIG. 12 shows an example of variations with time of the height of the tongue at the above described respective points P2 to P8 of the baby.

The variations with time are shown as an actual example when the baby sucks the breast milk. The vertical axis in FIG. 12 represents the height (mm), and the lateral axis represents time in seconds. The example in FIG. 12 contributes to know variations in height of the tongue in a certain lunar age, that is, variations in height and speed of the tongue. The data for other lunar ages can also be obtained in the same manner.

As shown in FIG. 12, the respective points P2 to P8 vary in different waveforms with time.

Returning back to FIG. 9, examples of height and speed relating to the variations of the tongue of the babies by lunar age are stored in the database DB1 of varying height of tongue by lunar age and the database DB2 of varying speed of tongue by lunar age, respectively. The varying height and speed of the tongue are obtained, for example, from the example shown in FIG. 12.

Examples of the strength and speed of the negative pressure that the baby can generate by lunar age are stored in the database DB3 of negative pressure strength by lunar age, and the database DB4 of speed of negative pressure by lunar age. The database DB3 of the negative pressure strength and the database DB4 of the speed of negative pressure are obtained by measuring variations in pressure using an artificial nipple attached with a pressure meter during suckling.

Example of the varied height and speed of the lower jaw of the baby by lunar age are stored in the database DB5 of varying height of lower jaw by lunar age, and the database DB6 of the varying speed of lower jaw by lunar age. These databases DB5, DB6 can be obtained from the example shown in FIG. 11C.

The respective databases DB1 to DB6 may be databases accumulated by weight, or may be databases accumulated both by lunar age and weight.

Figure 13:
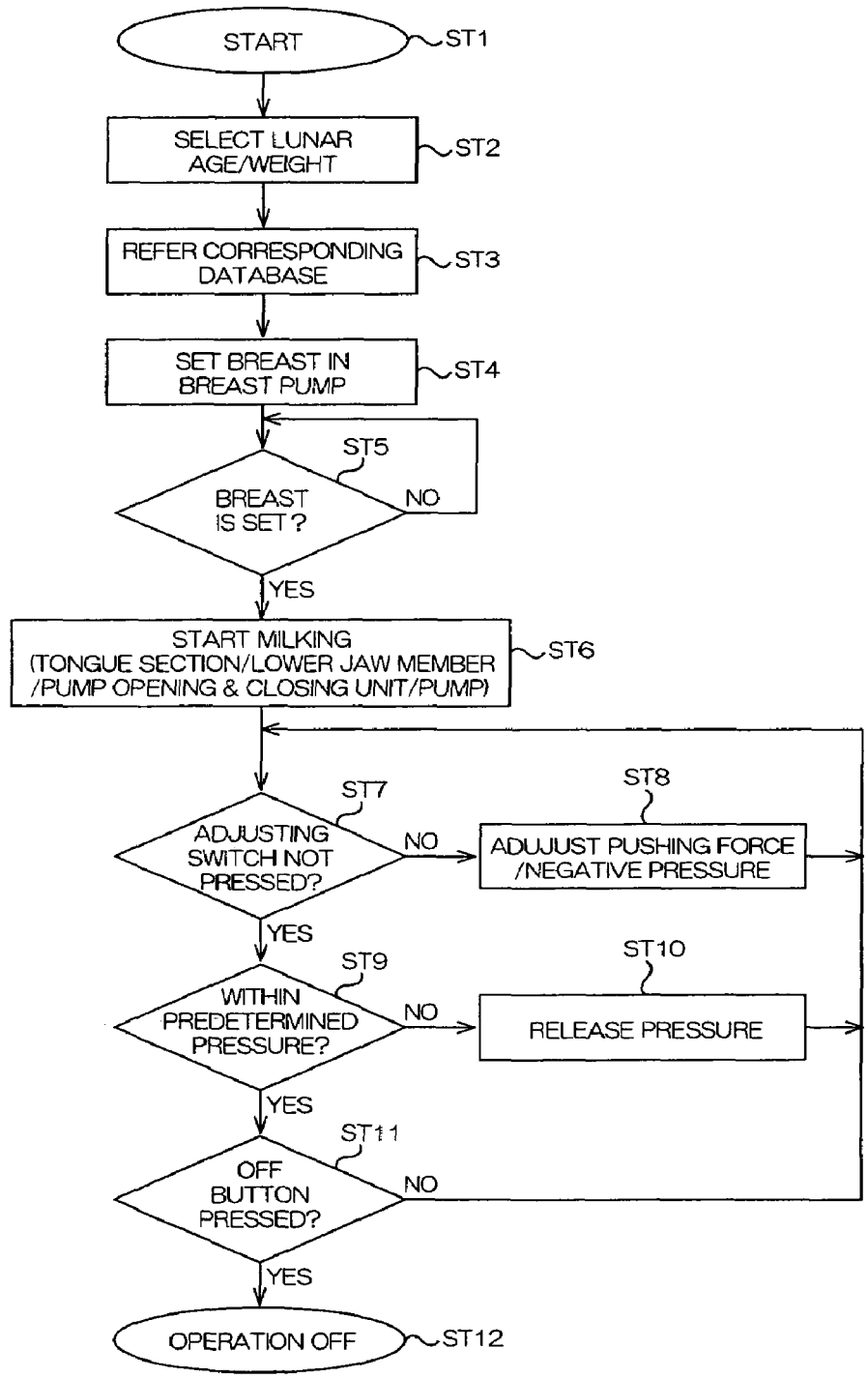
FIG. 13 is a flowchart showing an example of the action of the breast pump according to the invention.

Referring now to FIG. 13, an example of action of suckling of breast milk as the milking pump will be described.

In the flowchart shown in FIG. 13, steps from Step ST1 to Step ST12 are described.

In Step ST1, suckling action is started. The user selects the values of the lunar age and the weight of the baby using the lunar age/weight switch SW1 shown in FIG. 9 in Step ST2. At this time, it is adapted so that other setting values can be entered from the display input unit depending on the condition of the breast of the user, such as whether or not the breast is swelled up.

In Step ST3, the user refers the corresponding databases DB1 to DB6 from the drive information storage unit 200, and selects the varied height of the tongue, the varied speed of tongue, the strength of the negative pressure, the speed of the negative pressure, the varied height of the lower jaw, and varied speed of lower jaw by lunar age corresponding to the required lunar age.

Subsequently, in Step ST4, the user inserts the breast 300 into the contact member 77 and brings it into contact therewith. Accordingly, the papilla 400 is placed at a position between the upper jaw member 50 and the tongue member 60 on the lower jaw member 51. In this case, since the cushion member 78 supports the contact member 77, the degree of adhesion when the breast 300 is inserted into the contact member 77 can be secured and the feeling of the touch with respect to the breast 300 is softened to protect the breast 300 during milking.

Subsequently, in the Step ST5 in FIG. 13, whether the breast 300 is set into the milking port 23 as shown in FIG. 8 is determined. Determination whether or not the breast is set is done by the detection sensor 102 sending a detection signal to the control unit 100.

In Step ST 6 in FIG. 13, the milking action starts. In this case, the control unit 100 emits instructions for the operation of the motors M2 to M8, the operation of the lower jaw motor 115, the operation of the pump opening/closing motor M10, and the operation of the pump 24B.

In Step ST 7 in FIG. 13, when the user presses the adjusting switch SW2 in FIG. 9 because, for example, she feels a pain, the procedure goes to Step ST8. Accordingly, the control unit 100 adjusts the pressing force of the upper jaw member 50 and the lower jaw member 51 in FIG. 8 with respect to the papilla 400 in response to the pressing of the adjustment switch SW2. The control unit 100 also emits an instruction to the pump opening/closing motor M10 of the negative pressure generating unit 24 and the pump 24B in FIG. 6 to adjust the negative pressure in the case 20K.

When the adjusting switch SW 2 is not pressed in Step ST 7 in FIG. 13, the procedure goes to Step ST9. In Step ST9, it is determined whether the negative pressure in the case 20K in FIG. 8 is within a certain pressure. If the negative pressure exceeds a certain pressure, it is determined that the negative pressure is too high, and hence the negative pressure in the case 20K is released in Step ST10. After having completed the procedure in Step ST10, the procedure returns to Step ST7 again.

When the negative pressure in the case 20K is within an adequate certain pressure in Step ST9, the procedure goes to Step ST11. In Step ST11, whether or not the user has pressed OFF button for the operation of the breast pump is determined, and if yes, the operation is stopped in Step ST12.

With the operation as described above, the respective plate-shaped members 32 to 38 of the deforming device 30 can generate, for example, variations in height of the tongue (the peak of the tongue) with time as shown in FIG. 12 separately. In addition, the pulsated space of negative pressure by the negative pressure generating unit can be defined. With these movements, the papilla 400 is stimulated and hence the breast milk is expressed from the tip thereof into the case 20K of the milking unit 20 in FIG. 6. The breast milk expressed by the nipple 400 is stored in the storage 21 through the suction tube 24A. Since the storage 21 is a nursing bottle or a milking bag for freezing the breast milk, the extracted breast milk can be fed to the baby by the use of an artificial nipple or stored frozen.

The inventor found the following things in the suckling action. Relating to the tongue 500 or the points P2 to P8 of the tongue member 60 shown in FIGS. 7A and 7B and FIGS. 11A to 11C, the sucking and sipping intervals of the baby, that is, the time period required for the swelled portion of the tongue to move from the point P2 at the tip of the tongue to the point P8 as the inner side of the tongue, then disappear at the point P8 and appear at the point P2 tends to be shorter as the baby's lunar age increases.

Likewise, the peristaltic movement of the tongue to move from the point P2 to the point P8 tends to be shorter as the baby's lunar age increases. In other words, the time required for the wave of the tongue to move from the front half portion of the tongue to the rear half portion of the tongue becomes shorter with increase in lunar age, and this tendency of peristaltic movement is more obvious in comparison with the sucking and sipping intervals.

As regards swallowing, the time period required to move from the point P8 to the point P2 is shown. This time period tends to be longer with increase in lunar age. In other words, the time period required for swallowing, that is, the time period from the occurrence of swelling on the rear half of the tongue to the initiation of the subsequent wave on the front half portion of the tongue, tends to be longer with increase in lunar age.

The kinetic momentum of the tongue is different at the point P2, the point P5, and the point P8, respectively. For example, in the case of the baby up to about two months old, the kinetic momentum is larger at the point P8 than the point P2 and the point P5. It seems to be because the babies up to about two months old move with priority given to a reflex action.

In contrast, the babies from three months old on, optional movements of the tongue occur at the point P2, the point P5 and the point P8, and fluctuations in movements at the points P2, P5, and P8 increase, which means that they tend to do so called "drink-for-fun".

Regarding variations in cycle of the peristaltic movement or the peak, the smaller the lunar age of the baby is, the more regular movement he/she does. On the other hand, the larger the lunar age of the baby becomes, the more variations appear due to the tendency of drink-for-fun.

The databases DB 1 to DB6 stored in the drive information storage unit 200 reflect the above-described information, and hence the movement according to the stages of growth of the baby, such as the lunar age or weight can be reproduced.

It is also possible to store the information of the respective databases DB1 to DB6 accommodated in the drive information storage unit 200 in a card or the like, and allow the user to use the card of her own to provide such information as the lunar age or the weight to avoid necessity of setting the information such as the lunar age by herself as a matter of course.

In the embodiment of the invention, the pressure force of the tongue section of the milking unit can be controlled according to the program in the drive information storage unit. Therefore, breast milk can be extracted from the breast by selecting the program pattern according to the lunar age or the stage of growth (weight) of the baby to change the pressure of the tongue section. Therefore, by selecting an adequate pressing state of the tongue section, an adequate milking environment for the breast as an environment close to the actual suckling by the user's own baby can be reproduced.

In the embodiment of the invention, since the negative pressure generating unit generates negative pressure by pulsation corresponding to the variations in the milking unit, it can be adapted so that the negative pressure becomes higher before and after the timing when the pressing peak of the tongue section is moved to a tip most position of the nipple corresponding to the pressing by the tongue section.

According to the embodiment of the invention, since the actual expression of breast milk is significantly affected by a pressure stimulation by the tongue of the baby applied to a portion near the areola, the kinetic momentum can be provided so that the stimulation is applied at an adequate position and height by using the deforming device having the plurality of the sections.

The invention is not limited to the above-described embodiment.

In the above-described embodiment, the deforming device has a form divided into the plurality of sections using the plurality of plate-shaped members. The tongue member generates the peristaltic movement of the tongue member 60 by the vertical movement of the plate-shaped members 32 to 38, for example, in the direction Z in FIG. 7A.

However, the invention is not limited thereto, and the deforming device 30 may employ a structure in which a bag-shaped resilient member containing air therein is used to cause separate movement at the points P2 to P8 of the tongue member 60 by taking in and out air in the resilient bag instead of using a plurality of plate-shaped members as a matter of course.

In the embodiment of the invention, the deforming device 30 includes the plurality of plate-shaped members 32 to 38. These plate-shaped members 32 to 38 are rotated in the direction G about the centerline CL as shown in FIG. 2 to displace the position of the tongue member 60 by pressing the distal end 42 thereof against the inner side of the tongue member 60. In other words, by rotating the respective plate-shaped members 32 to 38 in the direction G about the centerline CL, desired displacement in the direction of height (direction Z) is generated at the points P2 to P8 of the tongue member 60.

In this arrangement, further accurate displacement of the tongue member 60 is achieved in comparison with a simple linear movement which displace the points P2 to P8 of the tongue member 60 in the direction Z (upper direction) from the inner surface of the tongue member 60. In other words, the transmitting portions 52 to 58 shown in FIG. 2 are formed so as to project in the radial direction about the centerline CL so that the power is transmitted by the rollers R2 to R8.

In this case, the transmitting portions 52 to 58 can positively transmit the force of the rollers via the teethed portions 59. By setting the radial length of the transmitting portions 52 to 58 and the radial length of the distal portions 42 adequately, a small power of the motor can be converted into the large displacement of the distal portions 42 in the direction G.

Since the motors M2 to M8 can be arranged while displaced along the circumference thereof by 30° in the example shown in FIG. 2, the motors can be arranged in the case 29 without interference with respect to each other. Since the plurality of plate-shaped members 32 to 38 are thin plate-shaped members such as metal or plastic, the thickness in the direction of the centerline CL can be reduced extremely.

The plate-shaped members 32 to 38 in FIG. 2 can directly adjust the displacement in the direction of height independently at the points P2 to P8 from the inner side of the tongue member 60 as shown in FIG. 7A. Accordingly, the tongue member 60 can adjust the height directly, and adjustment can be achieved easily and reliably. Since the respective plate-shaped members 32 to 38 can be adjusted in displacement separately by the motors M2 to M8 and rollers R2 to R8, delicate movement of the respective plate-shaped members 32 to 38 in the direction G can be reproduced again.

However, it is also possible to configure to move the plate-shaped members 32 to 38 in the vertical direction by independent piston movement, or the like, instead of circular movement, as a matter of course.

Although the above-described breast pump 10 is a floor model, and is adapted to receive the breast 300 inserted therein, it is also possible to employ a structure in which the motor or the like are selected as needed to cause the independent piston movement to configure the milking unit 20 to a compact size, whereby the user can use by holding the milking unit 20 with her hand.

In this manner, reflecting the study of the inventor relating the suckling, the breast pump according to the embodiment of the invention can reproduce the actual movement of the tongue of the baby by moving the peak of the tongue (also referred to as the pressing portion) stepwise.

Accordingly, the breast pump according to the embodiment of the invention can provide a stimulation of suckling of breast milk which is closer to the actual suckling by the baby to the nipple of the breast 300.

The invention is not limited to the above-described embodiment, and can be modified in various manners without departing the scope of appended claims.

The respective structures of the above-described embodiment can be partly omitted, or combined in a manner different from those shown above as needed.

What is claimed is:

1. A breast pump comprising:

a milking port which can accommodate a breast;

a storage for storing breast milk extracted from the breast; and a milking unit comprising a tongue section which can press a portion near an areola of the breast, wherein a peak height of the tongue section of the milking unit is configured to be moved continuously in a direction away from a side of the milking port, and the height of the tongue section is configured to be varied by independent and consecutive movements of a plurality of sections of a deforming device in a peristaltic manner from the side of the milking port to an inner side, wherein the tongue section is a continuous section that contacts the plurality of sections of the deforming device, and the plurality of sections of the deforming device are arranged adjacent to each other and along a same side of the tongue section and are independently driven.

2. The breast pump according to claim 1, comprising a negative pressure generating unit to generate a negative pressure at least in the milking port, wherein the negative pressure generating unit generates a negative pressure by pulsation according to variations in the milking unit.

3. The breast pump according to claim 1, wherein the milking unit includes a lower jaw member provided with the tongue section, so that the lower jaw member of the milking unit is adapted to be capable of varying the position in association with the movement of the peak of the tongue section.

4. The breast pump according to claim 1, wherein an upper jaw member to which upper surfaces of the breast, areola, and nipple come into contact is formed into a depressed shape that is partially spherical and located on the inner side in comparison with the side of the milking port.

5. The breast pump according to claim 1, wherein the plurality of sections of the deforming device are disposed in parallel.

6. The breast pump according to claim 1, wherein respective sections of the deforming device are connected to separate drive units so as to be capable of being displaced.

7. The breast pump according to claim 1, wherein protrusions of curved shape are formed on upper ends of the plurality of sections of the deforming device are configured as plate-shaped members which support the tongue section, so that the tongue section can be deformed upward by the protrusions in accordance with the upward displacement of the plate-shaped members.

8. The breast pump according to claim 1, wherein the tongue section includes a tongue member formed of a resilient material.

9. A breast pump comprising:
a milking port which can accommodate a breast;
a storage for storing breast milk extracted from the breast;
a milking unit including a tongue section which can press a portion near an areola of the breast; and
a deforming device located adjacent the milking unit and including a plurality of sections, the plurality of sections being movable with respect to each other,
wherein a peak height of the tongue section of the milking unit is configured to be moved continuously in a direction away from an outer side of the milking port, and the height of the tongue section is configured to be varied by independent consecutive movements of the plurality of sections of the deforming device, the deforming device sections arranged along a same side extending from the outer side of the milking port to an inner side of the milking port, wherein the tongue section is a continuous section that contacts the plurality of sections of the deforming device, and the plurality of sections of the deforming device are independently driven.

10. The breast pump according to claim 9, wherein the milking unit includes an upper jaw member that includes a depressed shape that is partially spherical and is located adjacent the inner side of the milking port.

11. The breast pump according to claim 9, wherein the tongue section includes a tongue member formed of a resilient material.

12. A breast pump comprising:
a milking port which can accommodate a breast;
a storage for storing breast milk extracted from the breast;
a milking unit including a tongue section which can press a portion near an areola of the breast; and
a deforming device located adjacent the milking unit and including a plurality of sections, the plurality of sections being movable with respect to each other,
wherein a peak height of the tongue section of the milking unit is configured to be moved continuously in a direction away from an outer side of the milking port, and the height of the tongue section is varied by independent consecutive movements of the plurality of sections of the deforming device from the outer side of the milking port to an inner side of the milking port, wherein the milking unit includes a movable lower jaw member provided with the tongue section, and an upper jaw member, the lower jaw member of the milking unit being configured to pivot with respect to the upper jaw member.

* * * * *